United States Patent
Busnach et al.

(10) Patent No.: US 7,112,281 B2
(45) Date of Patent: *Sep. 26, 2006

(54) UNDERDRAIN FOR FILTRATION MEMBRANE

(75) Inventors: Jeffrey S. Busnach, Billerica, MA (US); Brian Foley, Westford, MA (US); Phillip Clark, Wakefield, MA (US); Joseph E. Gabriels, Arlington, MA (US)

(73) Assignee: Millipore Corporation, Billerica, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 11/289,082

(22) Filed: Nov. 29, 2005

(65) Prior Publication Data

US 2006/0131237 A1 Jun. 22, 2006

Related U.S. Application Data

(62) Division of application No. 11/061,202, filed on Feb. 18, 2005, now Pat. No. 6,989,099, which is a division of application No. 09/565,963, filed on May 5, 2000, now Pat. No. 6,893,562.

(51) Int. Cl.
*B01D 29/92* (2006.01)

(52) U.S. Cl. .............. 210/650; 210/808; 210/248; 210/406; 210/474; 210/919; 422/101

(58) Field of Classification Search ............... 210/650, 210/767, 800, 808, 248, 406, 416.1, 474, 210/919
See application file for complete search history.

(56) References Cited

U.S. PATENT DOCUMENTS

| 3,888,629 | A | * | 6/1975 | Bagshawe .................. 436/541 |
| 4,246,339 | A | * | 1/1981 | Cole et al. .................... 435/5 |
| RE30,562 | E | * | 3/1981 | Park ....................... 435/287.2 |

(Continued)

FOREIGN PATENT DOCUMENTS

DE 197 53 849 6/1999

(Continued)

OTHER PUBLICATIONS

Copy of the European Search Report dated May 16, 2003.

*Primary Examiner*—Robert James Popovics
*Assistant Examiner*—T. Woodruff
(74) *Attorney, Agent, or Firm*—Nields & Lemack

(57) ABSTRACT

A device and method for removal of liquid from the downstream side of a membrane or a well, such as a well of a multiwell plate. More specifically, the present invention is directed to a wicking structure, which channels droplets of liquid away from a membrane in communication with a plurality of wells. In the preferred embodiment, the wicking structure is placed in a manifold.

2 Claims, 3 Drawing Sheets

U.S. PATENT DOCUMENTS

| | | | | |
|---|---|---|---|---|
| 4,427,415 A * | 1/1984 | Cleveland | ................... | 436/57 |
| 4,461,836 A * | 7/1984 | Von Froreich | ........... | 435/288.3 |
| 4,526,690 A * | 7/1985 | Kiovsky et al. | ............ | 210/335 |
| 4,734,192 A * | 3/1988 | Champion et al. | .......... | 210/335 |
| 4,777,021 A * | 10/1988 | Wertz et al. | ................ | 422/101 |
| 4,787,988 A * | 11/1988 | Bertoncini et al. | ......... | 210/808 |
| 4,797,259 A * | 1/1989 | Matkovich et al. | ......... | 422/101 |
| 4,833,087 A * | 5/1989 | Hinckley | ..................... | 422/58 |
| 4,895,706 A | 1/1990 | Root et al. | .................. | 422/102 |
| 4,902,481 A | 2/1990 | Clark et al. | ................. | 422/101 |
| 4,927,604 A | 5/1990 | Mathus et al. | .............. | 422/101 |
| 4,948,564 A | 8/1990 | Root et al. | .................. | 422/101 |
| 5,009,780 A | 4/1991 | Sarrasin | ..................... | 210/238 |
| 5,096,809 A * | 3/1992 | Chen et al. | ................... | 435/7.9 |
| 5,108,704 A * | 4/1992 | Bowers et al. | ................ | 422/70 |
| 5,141,719 A | 8/1992 | Fernwood et al. | .......... | 422/101 |
| 5,167,924 A | 12/1992 | Clask | ........................ | 422/101 |
| 5,244,630 A * | 9/1993 | Khalil et al. | .................. | 422/52 |
| 6,303,389 B1 | 10/2001 | Levin et al. | ................. | 422/101 |
| 6,592,815 B1 | 7/2003 | Zimmer | ....................... | 422/58 |
| 6,869,572 B1 * | 3/2005 | Kopaciewicz et al. | ...... | 422/101 |
| 6,893,562 B1 * | 5/2005 | Busnach et al. | ............ | 210/248 |
| 6,989,099 B1 * | 1/2006 | Busnach et al. | ............ | 210/650 |
| 2003/0132162 A1 * | 7/2003 | Busnach et al. | ............ | 210/650 |
| 2004/0247490 A1 * | 12/2004 | Olivier et al. | .............. | 422/101 |
| 2005/0145581 A1 * | 7/2005 | Busnach et al. | ............ | 210/790 |
| 2005/0161400 A1 | 7/2005 | Pitt et al. | .................... | 210/650 |
| 2005/0236317 A1 * | 10/2005 | Desilets et al. | ........... | 210/323.1 |
| 2005/0236318 A1 * | 10/2005 | Clark et al. | ............... | 210/323.1 |
| 2005/0236319 A1 * | 10/2005 | Emerick et al. | .......... | 210/323.1 |

FOREIGN PATENT DOCUMENTS

| | | |
|---|---|---|
| EP | 0 339 769 | 11/1989 |
| EP | 0 408 940 | 1/1991 |
| GB | 2 176 601 | 12/1986 |
| WO | 98/55852 | 12/1998 |

* cited by examiner

UNDERDRAIN FOR FILTRATION MEMBRANE

This application is a divisional of U.S. Ser. No. 11/061,202 filed Feb. 18, 2005, now U.S. Pat. No. 6,989,099 which is a divisional of U.S. Ser. No. 09/565,963 filed May 5, 2000, now U.S. Pat. No. 6,893,562, the disclosures of which are incorporated herein by reference.

BACKGROUND OF THE INVENTION

Test plates for chemical or biochemical analysis which contain a plurality of individual wells or reaction chambers are well known laboratory tools. Such devices have been employed for a broad variety of purposes and assays, and are exemplified in U.S. Pat. Nos. 4,734,192 and 5,009,780, for example. Microporous membrane filters and filtration devices containing the same have become especially useful with many of the recently developed cell and tissue culture techniques and assays, especially in the fields of virology and immunology. Multiwell plates, used in assays, often use a vacuum applied to the underside of the membrane as the driving force to generate fluid flow through the membrane.

Typically, a 96-well filtration plate is used to conduct multiple assays simultaneously. In the case of multiwell products, there is a need to deal with liquid collection, removal and recovery in an effective manner. In particular, high throughput applications, such as DNA sequencing, PCR product cleanup, plasmid preparation, drug screening and sample binding and elution require products that perform consistently and effectively. If droplets are allowed to remain in proximity to the purified sample for longer than necessary, a variety of deleterious effects may result, including possible contamination of purified sample.

One such filtration device commercially available from Millipore Corporation under the name "MULTISCREEN®" is a 96-well filter plate that can be loaded with adsorptive materials, filter materials or particles. The MULTISCREEN device underdrain has a phobic spray applied in order to facilitate the release of droplets. More specifically, the MULTISCREEN device includes an underdrain system that includes a spout for filtrate collection. This spout not only directs the droplets but also controls the size of the drops. Without the underdrain system, very large drops form across the entire underside of the membrane. The drop volume that can remain without such an underdrain is much larger than with such an underdrain. The spout is hydrophobically treated to enhance droplet release for quantitative collection.

It would therefore be desirable to provide an effective means for liquid collection in sample preparation devices such as multiwell arrays.

It would also be desirable to provide an effective means for removal of filtrate droplets from the underside of a membrane without requiring the addition of an underdrain system.

SUMMARY OF THE INVENTION

The problems of the prior art have been overcome by the present invention, which provides a device and method for removal of liquid from the downstream side of a membrane or a well, such as a well of a multiwell plate. More specifically, the present invention is directed to a wicking structure, which channels droplets of liquid away from a membrane or well, preferably a plurality of wells. In the preferred embodiment, the wicking structure is placed in a vacuum manifold in close proximity to the underside of the membrane or it can be an integral part of the manifold.

Since the presence of the wicking structure below the downstream side of the membrane effectively removes droplets of filtrate, contaminants in these droplets are channeled away from the membrane and are less likely to re-contaminate the sample through diffusion or osmotic forces, for example. Contamination of associated equipment, such as the robotic deck that the samples are processed on, is also less likely or eliminated. In addition, a wicking structure makes successive washes of samples on the upstream side of the membrane more efficient since contaminants are directed away from the underside of the membrane. The wicking structure is preferably used where quantitative collection of filtrate is not desired.

BRIEF DESCRIPTION OF THE DRAWINGS

FIG. 2b is a schematic view of a multi-well plate and manifold during filtration, wherein the wick is an integral part of the manifold, in accordance with the embodiment of FIG. 2a.

DETAILED DESCRIPTION OF THE INVENTION

Figure 1A:
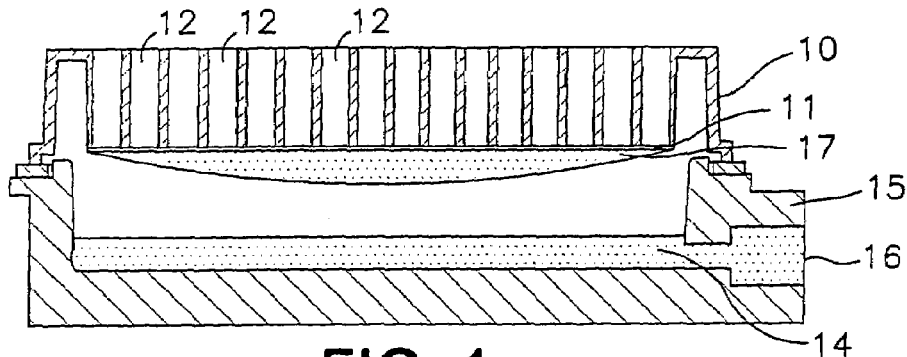
FIG. 1a is a schematic view of a conventional multi-well plate and manifold after filtration as taken place.

Turning first to FIG. 1a, there is shown a conventional plate and manifold assembly. Plate 10 includes a plurality of wells 12 to which is sealed a membrane 11, such as by heat-sealing, sealing with ultrasonics, solvents, adhesives, by diffusion bonding, etc. The type of membrane suitable is not particularly limited, and can include nitrocellulose, cellulose acetate, polycarbonate, polypropylene and polyvinylidene fluoride microporous membranes, or ultrafiltration membranes such as those made from polysulfone, polyvinylidene fluoride, cellulose or the like. A single membrane could be used, or where the sample preparation device is a plurality of wells, each well can contain or be in communication with its own membrane which can be the same or different from the membrane in communication with one or more of the other wells. The plate 10 is attached to a manifold 15, which includes a collection reservoir for collecting filtrate 14. The drive source for the filtration can be a vacuum source (not shown) connected via port 16. A positive pressure source (not shown) also could be used as the driving force, and would be applied to the liquid head above the filter.

A liquid droplet 17 is shown extending from the membrane 11. Removal of this liquid droplet 17 from the downstream side of the membrane 11 is desired to prevent contamination of other samples in the array as well as to prevent contamination of the robotic deck that these samples are processed on.

Figure 1B:
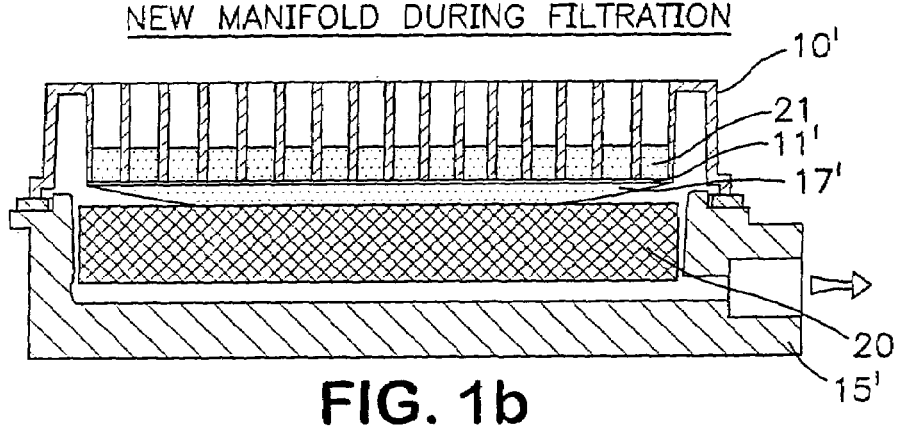
FIG. 1b is a schematic view of a multi-well plate and manifold with a wicking matrix during filtration in accordance with the present invention.

FIG. 1b illustrates a similar device with the wicking structure 20 of the present invention in place. The device is shown during the filtration process. Thus, sample to be filtered 21 is in the wells 12', and flows through the membrane 11' due to the action of gravity, a positive pressure source, and/or a vacuum source in communication with port 16'. As a liquid droplet 17' of filtrate forms, it contacts the wicking structure 20, is drawn by the wicking structure 20, and is therefore removed out of contact with the downstream side of membrane 11'. The filtrate is then generally discarded.

Figure 1C:
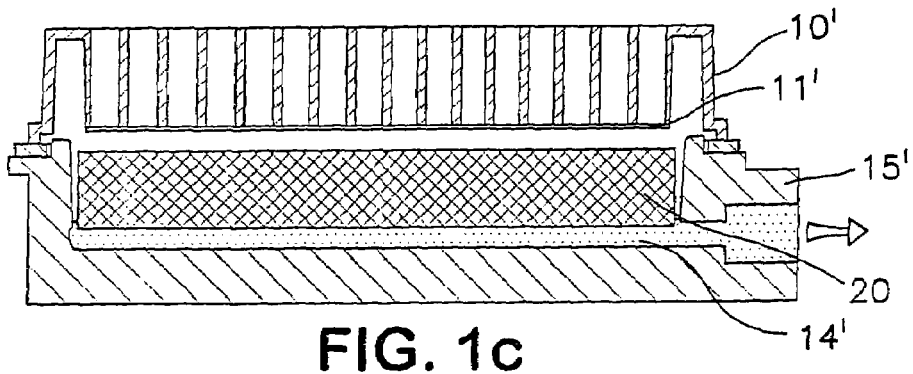
FIG. 1c is a schematic view of a multi-well plate and manifold with a wicking matrix after filtration in accordance with the present invention.

FIG. 1c shows the device of FIG. 1b after filtration is complete. Few, if any droplets remain on membrane 11'. Filtrate 14' seeps or is pulled by the vacuum from wicking structure 20 into the filtrate chamber, and can be discarded or reused, depending upon the application.

The wicking structure 20 is a conduit for the liquid to be drawn off the membrane and directed away from the membrane. In a preferred embodiment, the wicking structure 20 is an adsorbent material or matrix such as absorbent elastomeric, cellulosic or plastic material, including paper and nonwoven materials. One particularly suitable material is SCOTCH BRITE™ material. The wicking structure 20 can also be a non-absorptive material such as a metal rib positioned below the membrane. The structure 20 can be permanently positioned in the device of can be removable for cleaning and reuse, for elution, or it can be disposable. The wicking structure 20 also could be layers of the same or different absorbent material.

Where the wicking structure or matrix 20 is not in contact with the membrane surface, the gap between the wicking structure 20 and the membrane 11', must be sufficiently small to allow contact between the droplets of filtrate passing through the membrane 11' and the structure 20. Those skilled in the art will be able to readily determine the suitable positioning of the wicking structure 20, depending in part on the volume of sample being used and the surface tension of that sample. For example, in applications such as PCR where the total array volume is very small (10–100 μm), the wicking structure 20 and the underside of the membrane 11' must be in close proximity so that even the smallest volumes release from the membrane 11'. A suitable gap for this application is 0.5 mm, which ensures no migration of contaminants because the liquid is preferentially pulled into the structure 20 leaving an air gap. In some applications, the wicking structure 20 can contact the membrane 11', resulting in a gap of zero.

Figure 2A:
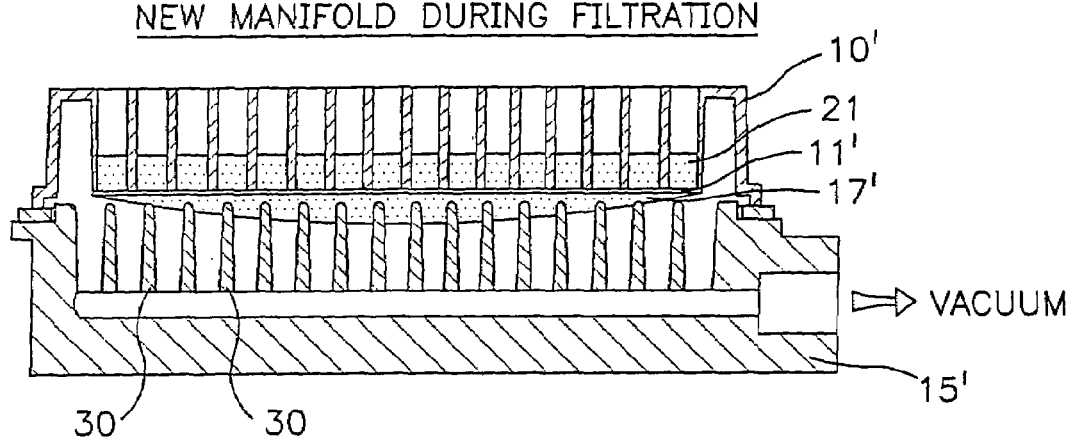
FIG. 2a is a schematic view of a multi-well plate and manifold during filtration, wherein the wick is an integral part of the manifold, in accordance with another embodiment of the present invention.
Figure 2B:
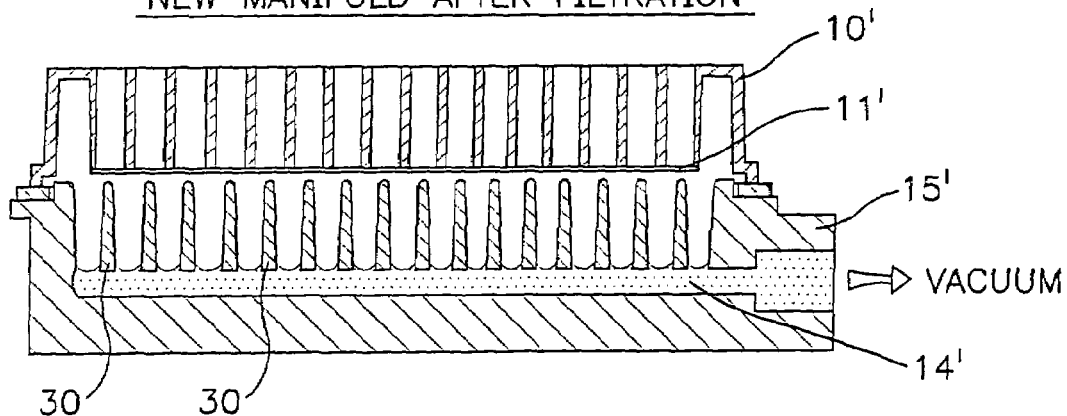
Figure 3:
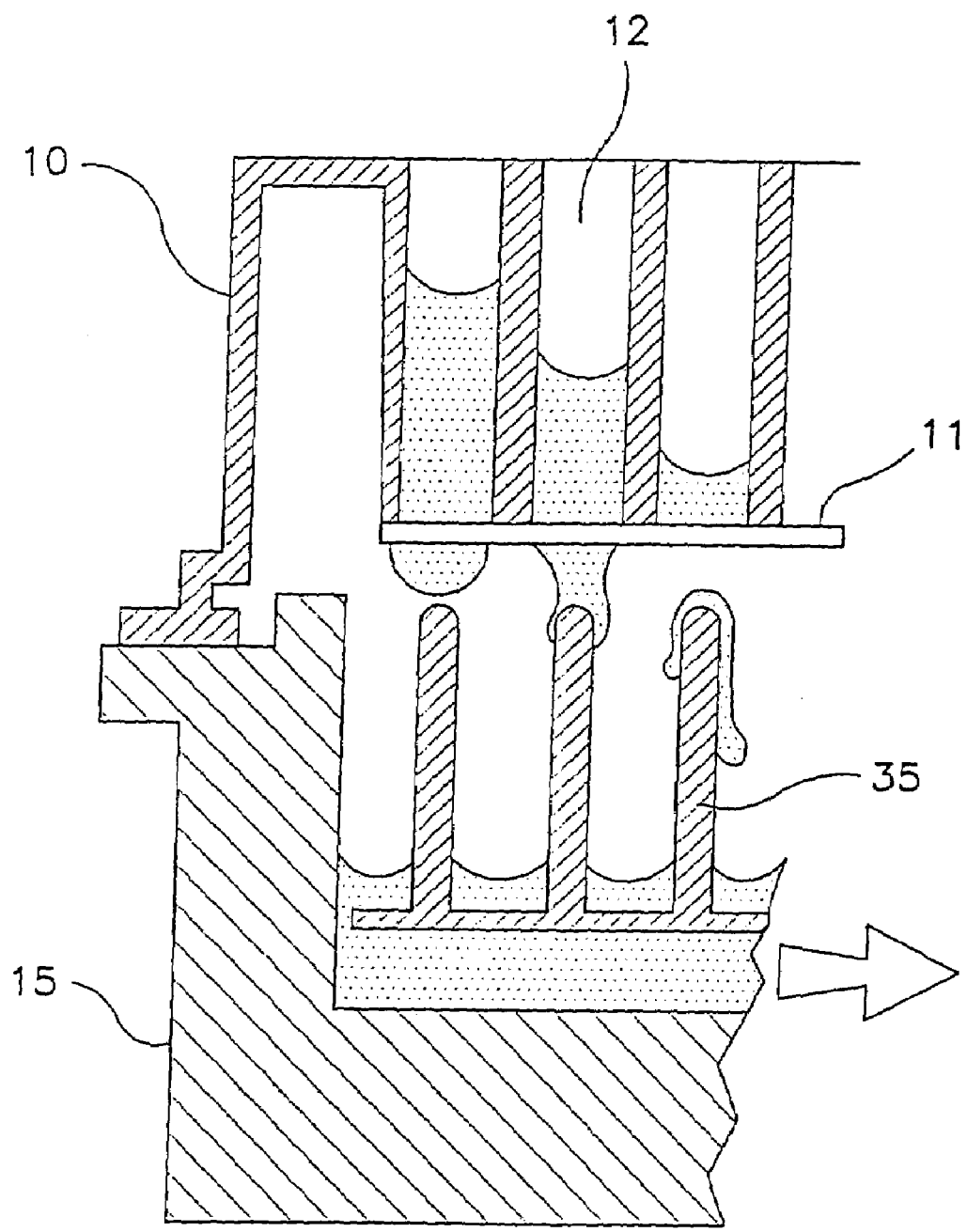
FIG. 3 is a partial schematic view of a multi-well plate and a manifold during filtration, wherein the wick is a plurality of pins in accordance with another embodiment of the present invention.

The configuration of the wicking structure 20 is not particularly limited. FIG. 2A shows an embodiment wherein the wicking structure 20' is an array of spaced ribs 30 positioned in the collection chamber of the manifold 15'. The ribs 30 extend in a direction from the collection chamber towards the membrane, and can taper towards their free end as shown. The ribs 30 contact the droplets 17' of liquid and direct them away from the membrane 11' and into the collection chamber (as filtrate 14') as shown in FIG. 2B. Preferably each rib 30 is positioned under the center of a well 12, and has a depth of greater than 1 mm.

In order to facilitate transfer of the droplet of filtrate from the surface of the membrane 11' to the wicking structure 20, 20', the membrane 11' can be rendered hydrophobic such as by treatment with a hydrophobic material such as a spray or the like. This helps isolate the droplets from one another, thereby producing a more consistent point of contact with the support, and yielding a release of the droplets to the more hydrophilic surface of the wicking structure 20, 20' leaving less residue on the membrane.

Regardless of the particular wicking structure used, the wicking structure functions to remove droplets formed from a plurality of sample wells into a single or common collection chamber. Segregation of the droplets forming from each well, and thus quantitative collection of the filtrate, is not required; droplets from all of the wells can be combined and collected together. The particular configuration of the common collection chamber is not particularly limited.

What is claimed is:

1. A method of filtering a liquid sample contained in a plurality of sample reservoirs, comprising:
    causing said sample to pass through a membrane in communication with each of said plurality of sample reservoirs to form a plurality of respective filtrates, said membrane having a membrane surface, each of said plurality of respective filtrates forming at least one droplet on said membrane surface;
    directing each of said at least one droplet from said membrane surface to a collection chamber by absorbing said droplet from said membrane surface, wherein each of said at least one droplet is directed from said membrane by an absorbent for said liquid.

2. The method of claim 1, further comprising providing a collection chamber for said plurality of filtrates, and providing means in said collection chamber for directing each of said one droplet from said membrane surface.

* * * * *